United States Patent [19]

Collier et al.

[11] Patent Number: 5,374,523
[45] Date of Patent: Dec. 20, 1994

[54] ALLELIC VARIANTS OF BOVINE SOMATOTROPIN GENE:GENETIC MARKER FOR SUPERIOR MILK PRODUCTION IN BOVINE

[75] Inventors: Robert J. Collier, University City; Scott D. Hauser, St. Louis; Gwen G. Krivi, Frontenac; Matthew C. Lucy, St. Louis, all of Mo.

[73] Assignee: Monsanto Company, St. Louis, Mo.

[21] Appl. No.: 926,785

[22] Filed: Aug. 10, 1992

[51] Int. Cl.$^5$ .................. C12Q 1/68; C12P 19/34; C07H 17/00

[52] U.S. Cl. ........................ 435/6; 435/91.1; 935/77; 935/78; 536/23.5; 536/23.51; 536/24.33

[58] Field of Search ............. 435/6, 91, 91.1; 935/78, 77; 536/27, 24.33, 23.5, 23.51

[56] References Cited

U.S. PATENT DOCUMENTS 5,041,371 8/1991 Cowan et al. .................. 435/6

FOREIGN PATENT DOCUMENTS

WO92/13102 8/1992 WIPO .

OTHER PUBLICATIONS

Seavey et al. Biochem. and Bioph. Regard Comm. 43(1) 189–195, 1971.
Eppard et al. Journal of Endocrinology 132: 47–56, 1992 (Jan.).
Large Dairy Herd Management, Wilcox et al. Eds. (1978).
M. C. Lucy, S. D. Hauser, P. J. Eppard, G. G. Krivi and R. J. Collier, "Genetic Polymorphism", American Dairy Science Association, 86th Annual Meeting, Aug. 12–15, 1991.
Abstract 30, Bovine Somatotropin (bST) gene polymorphism in Hereford bulls, H. M. Zhang et al. (1992).
Van Raden et al., "Derivation, Calculation, and Use of National Model Information" (1991) J. Dairy Sci 74:2737–2746.
C. R. Henderson, "Use of All Relatives in Intraherd Prediction of Breeding Values and Producing Abilities" (1975) J. Dairy Sci 58:1910–1916.
Massey et al., Genmark's Approach to Marker-Assisted Section, Animal Biotechnology 3 (1) 95–109 (1992).
Multi-Sire Pastures Single-Sire ID, Genmark Profile, Fall (1922) pp. 1, 3, 4.
Genetically Mapping the Future, Genmark (1991).
Genetically Mapping the Future, Genmark Profile, Spring 1992, pp. 1,3.
Milk Protein Analysis, Genmark (1991).
Weaver Testing, Genmark (1991).
The First Reliable Test for BLAD, Genmark (1991).
Bovine DNA Typing, Genmark (1991).
Embryo Cloning Accelerates Genetic Gains, Genmark (1991).

Primary Examiner—Margaret Parr
Assistant Examiner—Bradley L. Sisson
Attorney, Agent, or Firm—Gary M. Bond; George R. Beck

[57] ABSTRACT

An assay for determining the presence in bovine genetic material of a genetic marker located on the bovine somatotropin gene indicative of an inheritable trait of increased milk production is provided. The marker is a polymorphism in the gene encoding somatotropin at amino acid position 126 which results in two forms of somatotropin existing in bovine. The assay comprises analyzing a bovine to determine its genotype with respect to the somatotropin gene. Bovine with the desired marker can be selected for inclusion in breeding programs or for milking. The desired marker indicative of superior milk production is dependent upon the breed of cattle. Holstein cattle that are homozygous for the leucine forms of somatotropin are desired. Jersey cattle that are homozygous for the valine form of somatotropin are desired. A kit for performing the assay is also provided.

2 Claims, 2 Drawing Sheets

| Genotype | Number of cows (percent) | | | | | |
|---|---|---|---|---|---|---|
| | Brown Swiss | Holstein | Guernsey | Ayrshire | Jersey | |
| Leu/Leu | 26 (100) | 163 (85) | 5 (83) | 18 (58) | 25 (39) | |
| Leu/Val | 0 (0) | 28 (15) | 1 (17) | 13 (42) | 26 (41) | |
| Val/Val | 0 (0) | 0 (0) | 0 (0) | 0 (0) | 13 (20) | |
| Gene Frequency | | | | | | |
| Leu (p) | 1.0 | .93 | .92 | .79 | .59 | |
| Val (q) | .0 | .07 | .08 | .21 | .41 | |

FIGURE 1

| Genotype | Brown Swiss | | | Holstein | | | Guernsey | | | Ayrshire | | | Jersey | | |
|---|---|---|---|---|---|---|---|---|---|---|---|---|---|---|---|
| | N | Mean | SE | N | Mean | SE | N | Mean | SE | N | Mean | SE | N | Mean | SE |
| TA$_{milk}$ | | | | | | | | | | | | | | | |
| Leu/Leu | 13 | 549 | 95 | 39 | 1019 | 95 | 2 | 490 | 45 | 9 | 251 | 162 | 15 | 273 | 100 |
| Leu/Val | . | . | . | 9 | 650 | 199 | . | . | . | 8 | 26 | 172 | 27 | 244 | 74 |
| Val/Val | . | . | . | . | . | . | . | . | . | . | . | . | 10 | 598 | 122 |
| TA$_{fat\%}$ | | | | | | | | | | | | | | | |
| Leu/Leu | 13 | -.02 | .01 | 39 | -.03 | .02 | 2 | -.17 | .02 | 9 | .01 | .02 | 15 | -.01 | .03 |
| Leu/Val | . | . | . | 9 | .02 | .04 | . | . | . | 8 | .02 | .02 | 27 | .01 | .02 |
| Val/Val | . | . | . | . | . | . | . | . | . | . | . | . | 10 | -.04 | .04 |
| TA$_{prot\%}$ | | | | | | | | | | | | | | | |
| Leu/Leu | 13 | -.01 | .01 | 39 | -.04 | .01 | 2 | -.08 | .05 | 9 | -.01 | .01 | 15 | -.01 | .02 |
| Leu/Val | . | . | . | 9 | -.02 | .02 | . | . | . | 8 | .01 | .01 | 27 | .01 | .01 |
| Val/Val | . | . | . | . | . | . | . | . | . | . | . | . | 10 | -.01 | .01 |

FIGURE 2

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:1:

CCGTGTCTAT GAGAAGC          17

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

GTTCTTGAGC AGCGCGT          17

ALLELIC VARIANTS OF BOVINE SOMATOTROPIN GENE:GENETIC MARKER FOR SUPERIOR MILK PRODUCTION IN BOVINE

BACKGROUND OF THE INVENTION (1) Field of the Invention

This invention generally relates to bovine genetics and, more particularly, to a means for determining the presence of a genetic marker in bovine genetic material indicative of an inheritable trait of increased milk production.

(2) Description of the Related Art

A primary goal of the dairy industry has been to identify an efficient and economical way to increase milk production without increasing the size of the dairy herd. The traditional approach features breeding programs designed for the purpose of breeding and selecting dairy cows capable of superior milk production. While such programs have proved to be successful in improving milk production, they are disadvantageous because of the significant costs involved before the success of the program can be determined. For example, a traditional breeding program requires the breeding of many cows with a particular bull and subsequent analysis of the milk production of the female progeny of these cows to determine whether the bull is of superior genetic value. Of course, the female progeny must be raised, become pregnant, allowed to give birth and milked for a minimum length of time before its milk production capabilities can be analyzed. Thus, a breeding program relying on traditional techniques and selection criteria typically requires the investment of 4 or more years in a group of cattle before significant analysis of the program can be undertaken. It would, therefore, be advantageous if additional methods or criteria were available to determine whether a bull, heifer or cow should be included in a breeding program designed for superior milk production.

A technique utilized in genetic analysis known as restriction fragment length polymorphism analysis has been shown to be useful in identifying differences or polymorphisms in genetic material in a population. A polymorphism is an allelic variation in the genetic code of a particular gene sequence. That is, at least two different forms or variants of a gene sequence exist among subjects in a single population. It has been shown that some polymorphisms in a gene sequence can be identified by its association with recognizable differences in restriction fragment lengths when the gene sequence is cut by a particular restriction endonuclease. Thus, by analyzing numerous subjects within a population to determine the form of the gene existing in individual subjects, discrete groups within a population can be identified. These individual groups can then be compared to determine whether a variant of the gene is associated with a particular phenotype or trait.

Recently, researchers utilizing this type of analysis have identified a genetic marker indicative of superior milk production in bovine. The marker involves the presence of a polymorphism adjacent to the bovine prolactin gene sequence and a means for determining the presence of such polymorphism in bovine genetic material is described in U.S. Pat. No. 5,041,371. While this marker is useful in providing information regarding the genetic potential of a bovine for the purpose of breeding and selecting for superior milk production, it is acknowledged that it is just one piece of information to be considered in an overall breeding program. It would, therefore, be advantageous if other genetic markers in bovine genetic material could be identified that provide additional indication of the genetic potential of a bovine being considered for inclusion in a breeding program or in a milking herd. It would be desirable if, ultimately, a plurality of markers indicative of a desired trait in dairy cattle, such as superior milk production, could be identified and developed. This would provide the basis for a breeding and selection program requiring only the genetic analysis of a bovine to determine its genetic potential. Bovine that exhibited the desired genetic potential could then be selected for use in a breeding program based upon such genetic analysis.

Four variants of the bovine somatotropin gene are known to exist in cattle. (Wood et al. (1989) Purification and characterization of pituitary bovine somatotropin. J. Biol. Chem. 264:14741–14747) These variants arise from the combination of two possible N terminal amino acids (alanine or phenylalanine); See Lingappa et al. (1977) Nascent prehormones are intermediates in the biosynthesis of authentic bovine pituitary growth hormone and prolactin, Proc. Natl. Acad. Sci. 74:2432–2436) with two possible amino acids at position 126 of somatotropin (leucine or valine); See Seavey et al. (1971) Bovine growth hormone: evidence for two allelic forms. Bioch. Biophys. Res. Comm. 43:189–195). As used herein, the numbering of the somatotropin protein is with respect to the somatotropin having phenylalanine as its first amino acid. Variation at the N terminus of somatotropin arises from the variability in the cleavage of the signal peptide. This results in somatotropin molecules that are initiated by either alanine or phenylalanine. There is no known genetic element responsible for the variability in this cleavage event. On the other hand, allelic variation exists for the somatotropin molecule at amino acid position 126. This variation is caused by a single nucleotide change in the codon for amino acid 126 of the somatotropin gene.

Applicants are unaware of any reports associating the allelic variation of the bovine somatotropin gene at amino acid position 126 with the genetic potential for increased milk production. It is known that recombinant forms of the somatotropin protein can be injected into female cattle to increase milk production. It is also known that when Holstein dairy cattle are injected with recombinant forms of somatotropin to increase milk production, a greater response occurs in cows injected with the valine$_{126}$ variant as compared to the leucine$_{126}$ variant (Eppard et al. (1992) Comparison of the galactopoietic response to pituitary-derived and recombinant-derived variants of bovine growth hormone. J. Endocrinol. 132:47–56). It should be understood that the polymorphism in the somatotropin gene at amino acid position 126 provides a marker that can be correlated to the trait of superior milk production, but does not necessarily identify the polymorphism as the cause of such trait. The actual cause of the increased milk production may be due to some other closely linked (i.e. in close proximity) genetic factor or gene in the bovine's genome, and not to the existence of the polymorphism.

SUMMARY OF THE INVENTION

In one embodiment, this invention provides a novel assay for determining the presence in bovine genetic material of a genetic marker located on the bovine somatotropin gene indicative of an inheritable trait of increased milk production. The invention also provides a method for determining the genetic potential of a bovine for the trait of superior milk production by analyzing the bovine's somatotropin gene sequence for the existence of a desired genetic marker indicative of superior milk production. The marker is the heterogeneous nature of the somatotropin gene which is a result of a polymorphism in the somatotropin gene sequence that causes two forms of somatotropin to exist in the bovine population. One form expresses a leucine at amino acid position 126 of the somatotropin, and the other expresses a valine at that position. This assay is useful in analyzing the genetic potential of bulls and for the selection of genetically superior bulls for inclusion in a breeding program. The assay of this invention is also useful in identifying superior female cattle for milk production or for the identification and selection of superior mates to be used in a breeding program. This invention also finds utility in the selection of superior embryos for use in embryo transfer or for the determination of the lineage of cattle of unknown origin based on the frequency of the leucine and valine forms of somatotropin genes within the unknown cattle population.

The assay comprises identifying the bovine somatotropin gene from isolated bovine genetic material; exposing the gene to a restriction enzyme that yields restriction fragments of the gene of varying length; separating the restriction fragments to form a restriction fragment pattern, such as by electrophoresis or HPLC separation; and comparing the resulting restriction fragment pattern with a restriction fragment pattern from a bovine somatotropin gene that is either known to have or not have the desired marker. If a bovine tests positive for the desired marker, such bovine can be considered for inclusion in the breeding or milking program. If the bovine does not test positive for the desired marker, the bovine can be culled from the herd and otherwise used. The desired marker which is indicative of superior milk production is dependent upon the breed of cattle being tested. In Holsteins, cattle that are homozygous for the leucine form of somatotropin are preferred, whereas for Jerseys, cattle that are homozygous for the valine form of somatotropin are preferred.

In another embodiment, this invention provides a kit for assaying for the presence in bovine genetic material of a desired genetic marker located on the bovine somatotropin gene indicative of an inheritable trait of increased milk production. The kit includes oligonucleotide primers capable of amplifying a fragment of the bovine somatotropin gene that contains the polymorphism from bovine genetic material and a DNA sequence encoding bovine somatotropin that is known to either have or not have the desired genetic marker that can serve as the basis for determining the genotype of the subject bovine being tested. The kit may also include a suitable restriction endonuclease to obtain the gene fragments and reagents necessary to perform the amplification.

In a further embodiment of the invention, a method for determining the inclusion of a bovine in a breeding program designed to enhance the probability of increased milk production is provided. This method involves determining whether a desired genetic marker located on a gene encoding bovine somatotropin is present in bovine genetic material, the marker being indicative of an inheritable trait of increased milk production; and selecting only bovine that exhibit the desired genetic marker for inclusion in the breeding program. In particular, only those bulls carrying the desired marker are considered for inclusion in a sire program. Females are tested to determine their desirability as mates. Only those cattle that are homozygous for the marker would be selected. Female progeny could also be tested at birth to verify the presence of the marker. Only those carrying the desired marker would be raised to breeding age. This permits breeding decisions prior to milking age which lessens the cost of a breeding program and more quickly advances the breeding process.

Among the many objects of the present invention include the provision of an assay capable of identifying the presence of a desired genetic marker in bovine DNA associated with improved milk production; the provision of such an assay that can be used as a factor in the decision to include a bovine in a breeding or milking program; the provision of an assay useful in determining the genetic potential of a bovine relative to the trait of increased milk production that reduces the amount of time and money necessarily invested in such determination; the provision of such an assay that can be used in conjunction with a traditional breeding program or with other genetic markers; and the provision of a kit that quickly and easily determines whether a desired genetic marker which is useful in analyzing the genetic potential of a bovine for producing female progeny having superior milk production is present.

Other and further aims and objects of the invention will become apparent from the following description of the invention when viewed in conjunction with the drawing figures.

BRIEF DESCRIPTION OF THE DRAWINGS FIGURES

FIG. 1 illustrates the number of cows having one of three somatotropin genotypes (%) and the gene frequency of somatotropin alleles in cows representing five major dairy breeds.

FIG. 2 illustrates the mean and standard errors for transmitting abilities for milk, milk fat percentage, and milk protein percentage for cows from five dairy breeds with different genotypes for somatotropin.

DESCRIPTION OF THE PREFERRED EMBODIMENTS

In accordance with the present invention, a genetic marker located on the bovine somatotropin gene indicative of superior milk production in bovine has been discovered. The marker is a polymorphism in the gene encoding somatotropin at amino acid position 126. The marker can be identified using restriction fragment length polymorphism analysis. It has been found that, in Holsteins, the transmitting ability (TA) for milk production is greater for cows that are homozygous for the leucine$_{126}$ variant of somatotropin than cows that are heterozygous (leucine$_{126}$/valine$_{126}$) for the gene. In Jersey cows, it has been found that homozygous valine$_{126}$ cows are superior for milk TA. Thus, the desired marker for Holsteins is a somatotropin gene that is homozygous for the leucine$_{126}$ variant and the desired marker for Jerseys is a somatotropin gene that is homozygous for the valine$_{126}$ variant. Cattle can be analyzed according to the assay of this invention for somatotropin genotype and the results can be used in breeding and selecting cattle for use in a breeding program designed for increased milk production.

The term bovine as used herein includes the bovine itself or its gametes. The term "cattle" as used herein refers to both male and female bovines. The term "cow" as used herein refers to female cattle being used for milking and/or breeding and the term "heifer" as used herein refers to female cattle being used for breeding.

The assay of the present invention comprises, generally, identifying the bovine somatotropin gene from bovine DNA; exposing the somatotropin gene sequence to a restriction enzyme to yield restriction fragments of varying lengths; separating the restriction fragments by electrophoresis to form a restriction fragment pattern; and comparing the resulting restriction fragment pattern with a restriction fragment pattern from a bovine somatotropin gene that is either known to have or not have the desired marker. By comparison with a known restriction fragment pattern, the genotype of the bovine being tested can be determined.

The assay can be advantageously used with both male and female cattle. Bulls can be tested for their potential as sires to pass on the trait of superior milk production to female progeny. Therefore, preferred bulls exhibit a genotype that is homozygous for the desired marker for its breed. Heifers and cows can be analyzed for the potential of their ova to produce offspring capable of increased milk production and for their potential for superior milk production. As with bulls, preferred heifers and cows exhibit a genotype that is homozygous for the desired marker for its breed. Embryos can also be tested in order to assist in the selection of superior embryos (those that are homozygous for the desired marker) prior to embryo transfer.

The present invention is applicable for use with any breed of dairy cattle such as Holstein, Jersey, Brown Swiss, Ayrshire and Guernsey. As Holsteins and Jerseys are the most prominent breeds used in the dairy cattle industry, this invention has particular applicability to these breeds.

The somatotropin gene that carries the genetic marker of this invention can be identified from the genetic material, DNA or RNA, of the bovine being analyzed. Preferably, DNA from the blood or semen of the bovine is the source of the somatotropin gene sequence. The somatotropin gene can be identified from bovine DNA by methods known in the art such as those generally described in Sambrook, J., Fritsch, E. F., and Maniatis, T., Molecular cloning: A laboratory manual. (1989) Cold Spring Harbor Laboratory Press, Cold Spring Harbor, N.Y. Isolation of a gene from sperm can be performed generally by the method as described in Borenfreund, E., Fitt, E., and Bendich, A., Isolation and Properties of Deoxyribonucleic Acid From Mammalian Sperm, (1961) Nature vol. 191 pp. 1375-1377. Preferably, the somatotropin gene is isolated by amplification of the gene using polymerase chain reaction technology (PCR) using appropriate oligonucleotide primers. Of course, the somatotropin gene could be identified from genomic bovine DNA using hybridization and radio-labelled probe techniques or ligase chain reaction techniques, both of which are known to those skilled in the art. For exemplary purposes, the amplification of the somatotropin gene by PCR will be described.

It is known that two somatotropin genes exist in the bovine diploid genome and that both genes are transcribed and translated. Both gene sequences can be amplified and isolated by a single PCR reaction. The genomic map and sequence of bovine somatotropin is known. (Woychik et al. (1982) Cloning and nucleotide sequencing of the bovine growth hormone gene. Nucleic Acids Res. 10:7197-7210). Oligonucleotide primers were developed capable of amplifying and isolating a 428 base pair (bp) fragment of the bovine somatotropin gene that contained the polymorphism that serves as the genetic marker of this invention. The forward PCR primer is:

5'-CCGTGTCTATGAGAAGC-3'(SEQ ID NO.1);

and the reverse PCR primer is:

5'-GTTCTTGAGCAGCGCGT-3'(SEQ ID NO.2).

It is understood that other PCR primers could be developed or obtained that are also capable of amplifying a fragment of the somatotropin gene that contains the polymorphism.

It has been discovered that the polymorphism which causes the two variants of somatotropin at amino acid position 126 is a single nucleotide change in the codon for the amino acid at this position. In the leucine variant, the codon is CTG. In the valine variant, the codon is believed to be GTG. These variants result in restriction fragments of different lengths when exposed to particular restriction endonucleases. The AluI restriction enzyme is one such restriction endonuclease. AluI cuts double stranded DNA at the sequence 5'-AGCT-3'. The codon sequence of the leucine variant of the somatotropin gene at positions 125 and 126 is 5'-GAGCTG-3' and the codon sequence of the valine variant of the somatotropin gene at these same positions is 5'-GAGGTG-3'. The C to G change results in an amino acid coding change (Leu$_{126}$ to Val$_{126}$) and the loss of the AluI cut site. In particular, when the somatotropin gene is exposed to AluI, the leucine$_{126}$ variant forms restriction fragments of 265, 96, 51 and 16 base pairs in length and the valine$_{126}$ variant forms restrictions fragments of 265, 147 and 16 base pairs in length. The polymorphism is present in the 147 bp fragment. Therefore, cows that are homozygous for the leucine$_{126}$ variant gene exhibit DNA fragments of 265, 96 and 51 bp (the 16 bp fragment is not normally visible with traditional ethidium bromide staining techniques), heterozygous cows exhibit DNA fragments of 265, 147, 96 and 51 bp, and homozygous valine$_{126}$ cows exhibit DNA fragments of 265 and 147 bp. It should be understood that restriction endonucleases other than AluI that provide restriction fragments of varying length which correlate to and permit the identification of the presence of the polymorphism in the somatotropin gene can be used such as AlwNI or CviJI.

The resulting DNA fragments are separated, typically by gel electrophoresis, to yield a restriction fragment pattern. The restriction fragment pattern of the bovine subject being assayed is then compared to a known restriction fragment pattern to determine which variant of the somatotropin gene exists in the subject bovine. The known restriction pattern can be of a somatotropin gene that exhibits the desired marker or it can be of a somatotropin gene that does not exhibit the desired marker. Alternatively, the restriction fragment pattern of the bovine being assayed can be compared to known standard molecular weight markers.

The genotype with respect to the somatotropin gene of cattle from various breeds was determined in accordance with the assay of this invention. Holstein cows from the Cornell University (Ithaca, N.Y.) and Monsanto Company (Dardenne, Mo.) dairy herds were used. Brown Swiss, Ayrshire, Jersey and Guernsey cows were from the dairy herd at the University of Illinois (Champaign-Urbana, Ill.). The resulting restriction fragment patterns were analyzed and the genotypes and gene frequency of the somatotropin alleles in such cows is presented in FIG. 1.

Estimates of the genetic potential for milk production from cows whose genotype was determined was then analyzed to determine whether a correlation existed. These estimates were based on the transmitting abilities (TAs) for milk as determined by the Northeast ETA system for Holsteins or the USDA-PTA system for the other breeds. PTA stands for "predicted transmitting ability" and is used to evaluate the genetic merit of a cow or bull and its ability to transmit its genetic potential to its offspring. The numerical value assigned to a bovine as its PTA represents the number of pounds of milk a cow or a bull's daughters can be expected to produce over the average cow in the herd. A PTA value of zero indicates that a cow has the same genetic merit as the average milking cow in a tested herd. A PTA for a cow is based on three criteria: 1) The genetic potential of her parents; 2) her own ability to produce milk; and 3) the milk production of her daughters (Van Raden and Wiggans (1991) Derivation, Calculation and Use of National Animal Model Information. J. Dairy Sci. 74:2737-2746). Sires also have PTAs. PTAs are based on a 1990 base for average milk production of a cow. The ETA (estimated transmitting ability) is similar to PTA but also considers additional factors that affect milk production including herd and seasonal variations. ETA is based on a 1987 base for milk production (Henderson, C. R. (1975) Use of All Relatives in Intraherd Prediction of Breeding Values and Producing Abilities. J. Dairy Sci. 58:1910-1916).

A comparison of the genotype of the cows analyzed and their TAs showed that Holstein cows that were homozygous for the leucine$_{126}$ allele tended to have a greater TA for milk production than heterozygous Holstein cows. No valine$_{126}$ homozygous cows were identified in this study. Jersey cows that were homozygous for the valine$_{126}$ allele had greater TA as compared to heterozygous Jersey cows or leucine$_{126}$ homozygous Jersey cows. The TAs for milk fat percentage and protein percentages were similar among genotypes. This data is presented in FIG. 2. The values presented in FIG. 2 indicate the number of bovine analyzed (N), the estimated average advantage in number of pounds of milk produced by daughters of the bovine analyzed over the average cow (mean), and the standard error (SE). These results indicate a correlation between the genetic marker of this invention and a higher genetic transmitting ability for milk production in cows carrying the desired marker. It was determined that the data available for Brown Swiss, Guernsey and Ayrshire cows was insufficient in quantity to conclusively draw any correlation between genotype and milk production, but it is expected that a correlation would be obtained by analyzing more cows from those breeds according to the teachings of this invention.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example serves to illustrate the method by which the genotype of cattle analyzed in accordance with this invention was determined.

Approximately 10 ml of whole blood from a subject bovine was sampled into Vaccutainer tubes containing 10.5 mg EDTA. The blood was mixed and frozen at $-20°$ C. until analysis. Two hundred and fifty $\mu l$ of whole blood from each cow was mixed with 750 $\mu l$ of blood lysis buffer (0.32M sucrose, 10 mM Tris-HCl pH7.5, 5 mM MgCl$_2$, 1% Triton X-100), vortexed for 5 seconds and centrifuged in a microfuge at 12,000 xg for 20 seconds. The supernatant was decanted, and the pellet was resuspended in 1 ml of blood lysis buffer, centrifuged at 12,000 xg for 20 seconds and the supernatant decanted. This wash step was repeated once more and the pellet was resuspended in 250 $\mu l$ of NIDPCR buffer (50 mM KCl, 10 mM Tris-HCl pH 8.3, 2.5 mM MgCl$_2$, 0.1 mg/ml gelatin, 0.45% nonidet P40, 0.45% Tween 20). Thirty $\mu g$ of Proteinase K (Fisher BioTech, Fairlawn, N.J., U.S.A.) was added to each sample and samples were then incubated for one hour at 50° C.

Following the Proteinase K digestion, samples were extracted twice with TE buffer (10 mM Tris-HCl, 1 mM EDTA, pH 7.4)-saturated phenol:chloroform (1:1) followed by two extractions with chloroform. The DNA was precipitated with two volumes of 100% ethanol, and 0.1 volume of 3M sodium acetate, and pelleted by centrifugation (15 minutes at 12,000 xg). The DNA was washed once with 70% ethanol, dried and resuspended in 20 $\mu l$ of distilled water.

A polymerase chain reaction (PCR) was then conducted on the DNA extracted from the whole blood sample to amplify the somatotropin gene. Fifty $\mu l$ PCR were carried out in 0.6 ml PCR reaction tubes. Five $\mu l$ of the extracted DNA solution was added to 30 ml of H$_2$O, 5 $\mu l$ of 10x PCR buffer (100 mM Tris-HCl, pH8.3, 500 mM KCl, 15 mM MgCl$_2$, 0.01% gelatin), 1 $\mu l$ 10 mM dATP, 1 $\mu l$ 10 mM dCTP, 1 $\mu l$ 10 mM dGTP, 1 $\mu l$ 10 mM dTTP, 5 $\mu l$ of the forward PCR primer (5'-CCGTGTCTATGAGAAGC-3' (SEQ ID NO. 1); 10 pmol/l; Midland Certified Reagent Co., Midland, Tex., U.S.A.), 5 $\mu l$ of the reverse PCR primer (5'-GTTCTTGAGCAGCGCGT-3' (SEQ ID NO. 2); 10 pmol/l), and 0.25 $\mu l$ of TAQ DNA polymerase (Perkin-Elmer Amplitaq® DNA polymerase, 5 units/$\mu l$, Roche Molecular Systems, Inc., Brachburg, N.J., U.S.A.). This mixture was vortexed and overlayed with two drops of mineral oil prior to amplification. Amplification was carried out in a Perkin-Elmer DNA thermalcycler. Programmed cycles were: one cycle at 94° C. for 10 minutes, and 30 cycles at 94° C. for 30 seconds, 60° C. for 60 seconds, and 72° C. for 30 seconds. The primers were designed to amplify a 428 bp fragment of the somatotropin gene. The resulting DNA contains significant amounts of the desired fragment of the somatotropin gene. This DNA can be stored at 4° C. until analysis.

The somatotropin gene PCR product was analyzed by exposing the somatotropin gene sequence to one unit of AluI restriction enzyme (New England Biolabs, Beverly, Mass., U.S.A.) in 5 $\mu l$ of buffer (100 mM NaCl, 10 mM Tris-HCl, pH 7.5, 10 mM MgCl$_2$, 100 $\mu g$/ml bovine serum albumin) which was mixed with 35 $\mu l$ of PCR reaction and incubated at four hours at 37° C.

Following digestion, the samples were dried down to 10 μl of total volume, mixed with gel loading buffer (0.25% bromophenol blue, 0.25% xylene cyanol FF, 30% glycerol in water) and electrophoresed through a 5% low melting agarose gel (Fisher Biotech) in 1x TBE buffer (0.09M Tris-Borate, 0.002M EDTA) and ethidium bromide (1.25 μM). The genotype was determined from sizes of restriction fragments by comparison with DNA molecular weight markers and by comparison with a restriction fragment pattern of a bovine somatotropin gene of known genotype.

EXAMPLE 2

This example serves to illustrate the correlation of the desired genetic marker of this invention with the TA for milk production for Holsteins and Jerseys.

The somatotropin genotype of 48 Holsteins and 52 Jerseys were determined as described in Example 1. The TAs of these cattle were determined from available ETA and PTA values for the cattle. The data is tabulated in FIG. 2. Holsteins that were homozygous for the leucine$_{126}$ variant had a TA of 1019 pounds of milk as compared to 650 pounds for a heterozygous Holstein. This represents about a 2% increase in milk production for homozygous cows. The probability of a Type I error for the comparison of the TAs of homozygous leucine Holsteins versus heterozygous Holsteins is 0.1.

For Jerseys, a cow that is homozygous for the valine$_{126}$ variant exhibited a TA of 598 pounds of milk. Homozygous leucine Jersey and heterozygous Jersey cows had TAs of 275 pounds of milk and 244 pounds of milk, respectively. This represents about a 2% increase in milk production for homozygous valine Jerseys as compared to those of other genotypes. The probability of a Type I error for the comparison of TAs of homozygous valine Jerseys versus heterozygous or homozygous Jerseys is 0.05.

EXAMPLE 3

This example serves to illustrate the correlation between the genetic marker and increased milk production in Holsteins.

The somatotropin genotype of 142 Holsteins from a dairy herd (Monsanto Co., Dardenne, Mo.) was determined as described in Example 1. One hundred twenty-three of the cows were homozygous for the leucine$_{126}$ variant and 19 were heterozygous for the somatotropin gene. The milk produced by these cows was measured during a first or second lactation period.

The mean value of milk produced by cows that were heterozygous for the somatotropin gene was 18,924.2 lbs. The mean value of milk produced by cows that were homozygous for the leucine$_{126}$ variant was 19,417.9 lbs. Thus, a difference of over 440 lbs. of milk produced was evident in cows of the homozygous leucine$_{126}$ genotype. The number of cows analyzed in this Example was insufficient to provide a sensitive test of milk production for homozygous leucine and heterozygous Holsteins, but the data indicates a numerically greater milk production in homozygous leucine Holsteins as compared to heterozygous Holsteins.

---

---

What is claimed is:

1. A method for determining the inclusion of a Holstein bovine in a breeding program designed to enhance the probability of increased milk production in female progeny, said method comprising:

assaying genetic material from said Holstein bovine to determine whether a genetic marker located on a gene encoding bovine somatotropin in said bovine genetic material is present, said marker being selected from polymorphisms in said gene in a codon coding for the amino acid at position 126 of somatotropin and indicative of an inheritable trait of increased milk production; and selecting for inclusion in said breeding program bovine that exhibit said genetic marker;

wherein said genetic marker of said gene is homozygous leucine$_{126}$ alleles.

2. A method for determining the inclusion of a Jersey bovine in a breeding program designed to enhance the probability of increased milk production in female progeny, said method comprising:

assaying genetic material from said Jersey bovine to determine whether a genetic marker located on a gene encoding bovine somatotropin in said bovine genetic material is present, said marker being selected from polymorphisms in said gene in a codon coding for the amino acid at position 126 of somatotropin and indicative of an inheritable trait of increased milk production; and selecting for inclusion in said breeding program bovines that exhibit said genetic marker;

wherein said genetic marker of said gene is homozygous valine$_{126}$ alleles.

* * * * *